United States Patent
Zaromb

(10) Patent No.: US 6,762,060 B1
(45) Date of Patent: *Jul. 13, 2004

(54) APPARATUS AND METHODS FOR MONITORING THE CONCENTRATIONS OF HAZARDOUS AIRBORNE SUBSTANCES, ESPECIALLY LEAD

(76) Inventor: Solomon Zaromb, 9S 706 William Dr., Hinsdale, IL (US) 60521

( * ) Notice: Subject to any disclaimer, the term of this patent is extended or adjusted under 35 U.S.C. 154(b) by 0 days.

This patent is subject to a terminal disclaimer.

(21) Appl. No.: 08/377,966

(22) Filed: Jan. 25, 1995

Related U.S. Application Data

(63) Continuation-in-part of application No. 08/255,712, filed on Jun. 7, 1994, now abandoned, and a continuation of application No. 07/931,572, filed on Aug. 10, 1992, now abandoned, which is a continuation-in-part of application No. 07/993,080, filed on Dec. 18, 1992, now Pat. No. 5,328,851, which is a division of application No. 07/499,602, filed on Mar. 26, 1990, now Pat. No. 5,173,264, which is a continuation-in-part of application No. 07/330,654, filed on Mar. 30, 1989, now Pat. No. 4,942,135, and a continuation-in-part of application No. 07/330,655, filed on Mar. 30, 1989, now Pat. No. 4,977,095.

(51) Int. Cl.$^7$ ................................................ G01N 1/18
(52) U.S. Cl. ......................... 436/178; 436/52; 422/69; 422/88; 55/423
(58) Field of Search .............................. 422/52, 56, 88, 422/91, 89, 98, 69; 436/52–55, 165, 167, 178, 168, 172, 909, 161, 169; 55/161, 158, 167, 423

(56) References Cited

U.S. PATENT DOCUMENTS 5,173,264 A * 12/1992 Zaromb et al. ............... 422/88

OTHER PUBLICATIONS

Microgon Inc., "MiniKap 225/500 Microfiltration Modules", Jul. 1990.*
DeAngelis et al. "Differential Pulse Anodic Stripping Voltammetry in a Thin–Layer" Analytical Chemistry, vol. 48, No. 14, Dec. 1976.*
Gunasingham et al. "Computer Automation of Anodic Stripping Voltammetry with a Mercury Film Wall—Jet Electrode", J. Electroanal. Chem. 186(1985) 51–61.*
Heijne et al. "The Formation and Properties of Mixed Lead Sulfide–Silver Sulfide Membranes for Lead(II)–Selective Electrodes" Analytica Chimica Acta, 100(1978) 193–205.*
Fleet et al., "Performance and Evaluation of a Handheld Electrochemical Monitor for Toxic Metals", No Source or Publication Date Supplied.*

(List continued on next page.)

Primary Examiner—Lyle A. Alexander
(74) Attorney, Agent, or Firm—Solomon Zaromb

(57) ABSTRACT

Air is sampled at a rate in excess of 100 L/min, preferably at 200–300 L/min, so as to collect therefrom a substantial fraction, i.e., at least 20%, preferably 60–100%, of airborne particulates. A substance of interest (analyte), such as lead, is rapidly solubilized from the the collected particulates into a sample of liquid extractant, and the concentration of the analyte in the extractant sample is determined. The high-rate air sampling and particulate collection may be effected with a high-throughput filter cartridge or with a recently developed portable high-throughput liquid-absorption air sampler. Rapid solubilization of lead is achieved by a liquid extractant comprising 0.1–1 M of acetic acid or acetate, preferably at a pH of 5 or less and preferably with inclusion of 1–10% of hydrogen peroxide. Rapid determination of the lead content in the liquid extractant may be effected with a colorimetric or an electroanalytical analyzer.

19 Claims, 4 Drawing Sheets

OTHER PUBLICATIONS

Lawson et al., "Evaluation of Chemical Reaguts For Quick Estimation of Air–Borne Lead Concentrations", NCEL Contract Report (CR91.009), Aug. 1991.*

Zaromb et al., "Portable High–Throughput Liquid–Absorption Air and Aerosol Sampler" Abstract Present at the Haztech Int.Conf. Pittsburgh, Pa. 5/14–16/91.*

Product cover letter col Product Lit. of "MinikKap 225/500" from Microgon, Inc., Laguna Hills, Ca. (No Date).*

Oakton Electrascon (EC–1 Series) product liteture with a price list effective Mar. 1, 1991.*

* cited by examiner

APPARATUS AND METHODS FOR MONITORING THE CONCENTRATIONS OF HAZARDOUS AIRBORNE SUBSTANCES, ESPECIALLY LEAD

REFERENCE TO RELATED APPLICATIONS

This is a continuation of application Ser. No. 07/931,572, filed Aug. 10, 1992 ABN, and a continuation-in-part of application Ser. No. 08/255,712, filed ABN Jun. 7, 1994, both of which are continuations-in-part of application Ser. No. 07/993,080, now U.S. Pat. No. 5,328,851, which was a divisional application of application Ser. No. 07/499,602, filed Mar. 26, 1990, now U.S. Pat. No. 5,173,264, which was a continuation-in-part of U.S. applications Ser. No. 07/330,654, filed Mar. 30, 1989, now U.S. Pat. No. 4,942,135, and Ser. No. 07/330,655, filed Mar. 30, 1989, now U.S. Pat. No. 4,977,095. The disclosures of all of said applications and patents are incorporated herein by reference.

CONTRACTUAL ORIGIN OF THE INVENTION

The U.S. Government has rights in this invention pursuant to Contract No. W-31-109-ENG-38 between the U.S. Department of Energy and the University of Chicago representing Argonne National Laboratory.

BACKGROUND OF THE INVENTION

This invention relates to apparatus and methods for monitoring the concentrations of hazardous airborne substances, especially lead in fire ranges, in and around lead-smelting or lead-fabricating facilities, lead-acid battery or pottery and ceramic plants, radiator repair and other soldering shops, dwellings contaminated with chipping lead paint, and other locations were elevated respirable levels may pose a hazard to human health.

According to recent estimates, in the State of California alone, almost 400,000 workers have elevated lead blood levels, of which some 60,000 persons may have potentially toxic lead levels. Similar data from Texas, New York, and New Jersey, "show that there is an epidemic of occupational lead poisoning in the United States" (Chicago Tribune, Aug. 30, 1990, Sec. 1, Page 4).

It is therefore the purpose of this invention to provide a cost-effective method and instrumentation for monitoring airborne lead concentrations in said locations to help prevent lead poisoning among exposed persons. The need for "practical, low-cost ways of monitoring lead concentrations at firing ranges" has been well recognized (D. J. Schaeffer, R. A. Deem, and E. W. Novak, Am. Ind. Hyg. Assoc. J., 51(2):84–89 (1990)). The Occupational Safety and Health Administration's permissible exposure limit to airborne lead is a concentration of $5 \times 10^{-5}$ g Pb/m$^3$ averaged over an 8-hour period. An experimental ambient-air lead monitor based on X-ray fluorescence spectrometry has demonstrated a detection capability of $5 \times 10^{-5}$ g Pb/m$^3$ in 40–60 min and of higher concentrations in shorter times. Comparable or longer periods of time are required by the present NIOSH Method 7082 (issued by the National Institute of Occupational Safety and Health on Feb. 15, 1984), which is based on atomic absorption spectroscopy. The NIOSH method calls for a sampling flow rate of 1–4 L/min and a minimum volume of 200 L, which necessitates a minimum sampling time of 200 L/4 L-min$^{-1}$ =50 min. It is thus obvious that shorter sampling times and higher detection sensitivities are needed for more cost-effective lead monitoring.

It is therefore another object of this invention to provide an inexpensive, portable, and rapid means for estimating airborne lead concentrations.

Other objects of the invention will become apparent to professionals in the health monitoring, industrial safety and hygiene, environmental, metallurgical, and related areas following perusal of the complete specification.

SUMMARY OF THE INVENTION

Briefly, the invention consists of sampling air at a rate in excess of 100 L/min, preferably at 200–300 L/min, and collecting therefrom a substantial fraction, i.e., at least 20%, preferably 60–100%, of airborne particulates, rapidly solubilizing the hazardous substance of interest (analyte), such as lead, from the collected particulates into a sample of liquid extractant, and determining the concentration of the analyte in the extractant sample. The high-rate air sampling and particulate collection may be effected with a high-throughput filter cartridge or with a recently developed portable high-throughput liquid-absorption air sampler, wherein an asymmetric air inlet is so designed as to impart a partly downward and rotational motion to the in-rushing air. Rapid solubilization of lead is achieved by a liquid extractant comprising 0.1–1 M of acetic acid or acetate, preferably at a pH of 5 or less and preferably with inclusion of 1–10% of hydrogen peroxide. Rapid determination of the lead content in the liquid extractant may be effected with an indicator tape or an electrochemical analyzer.

BRIEF DESCRIPTION OF THE DRAWING

The invention is best explained with reference to the drawings, in which.

DESCRIPTION OF THE PREFERRED EMBODIMENTS

Figure 1:
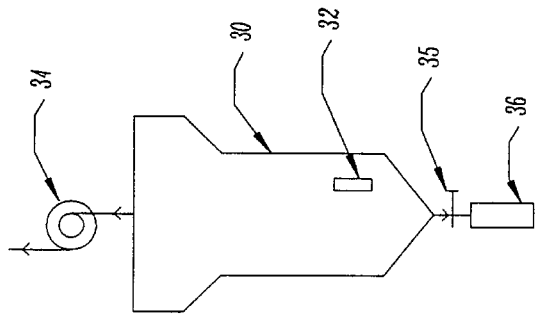
FIG. 1 is a block diagram of a system for monitoring hazardous substances.

As indicated in the block diagram of FIG. 1, the invention comprises the following three broad key elements:
 a high-throughput air sampler and particulate collector 1;
  a means 3 for solubilizing the analyte that is contained in the collected particulates; and
 an analyte detection means 5. The sampler and collector 1 may be combined with the solubilizer 3 into a single device, as shown in FIGS. 2 and 3.

Figure 2:
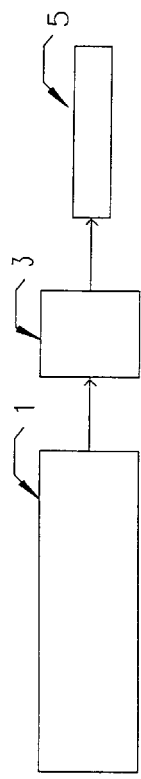
FIG. 2 is one variant in which the elements 1 and 3 of FIG. 1 are combined in a single device.

In FIG. 2, a high-throughput filter cartridge module 2 combines the functions of elements 1 and 3. For instance, a "MiniKap 500 Microfiltration Module" that is marketed by Microgon, Inc., Laguna Hills, Calif. 92653, comprises isotropic, hydrophilic, hollow-fiber membranes with an effective filtration area of 500 cm$^2$ that retains particulates larger than 0.2 microns in size. Its rated air flow is 130 L/min at an applied pressure differential of 0.7 atm between the air inlet 7 and air outlet 9 of cartridge module 2. The required pressure difference is effectuated by an air pump 11, which draws the filtered air out of cartridge 2 into an exhaust 12.

The MiniKap 500 module has a hold-up volume of 37 mL, which means that 37 mL of liquid extractant will suffice to solubilize any lead or other analyte of interest that is collected by the hollow-fiber membranes. Thus, after sampling air and collecting the airborne particulates for a measured length of time, say 1–3 minutes, the liquid extractant 13 is drawn from a reservoir 15 by a liquid-metering pump 17 and fed into module 2 through a liquid inlet 19 until the module is filled with the liquid. After soaking the filter cartridge for a predetermined time interval, e.g., 1 or 2 minutes, the analyte-enriched extractant is pumped out of module 2 through a liquid exit 21, and a portion of that extractant is fed to the inlet 23 of an analyzer 25 and discarded at the analyzer outlet 26. The excess portion of the analyte-enriched extractant can be discarded too via outlet 22.

Figure 3:
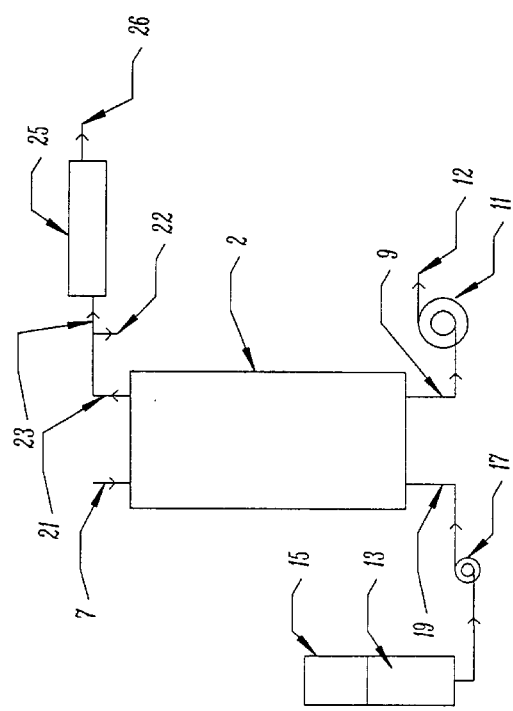
FIG. 3 is another variant in which the same elements are combined in an alternative device.

In the alternative embodiment of FIG. 3, the filter cartridge 2 of FIG. 2 is replaced by a recently developed variant of the high-throughput liquid-absorption sampler (HTLAAS) disclosed in my U.S. Pat. No. 4,977,095, dated Dec. 11, 1990, and my copending application Ser. No. 07/499,602, filed Mar. 26, 1990. The HTLAAS offers unique advantages in rapid detection and analysis of trace air contaminants. Its advantages result from (a) a high air sampling rate (0.6–0.8 m$^3$/min), (b) an analyte collection efficiency of 30–60%, and (c) a low volume of collected liquid sample ($\cong$1–2 mL). All of these features combine to concentrate the analyte from a large volume of air into a small volume of liquid and thereby reduce the effective LDL (lower detection limit) of available analytical methods by a large factor and/or permit faster sampling and far more rapid on-site analyses than were previously feasible. The small volume of collected liquid renders the HTLAAS readily adaptable to various water analyzers, such as colorimetric or electro-analytical detectors.

Also disclosed in my copending application Ser. No. 08/255,712, filed Jun. 7, 1944, is a portable, downscaled version of the HTLAAS weighing <2 Kg, including a power pack, and having a throughput of >200 L/min. This device is represented here by the arrow-like block 30 of FIG. 3.

To operate the system of FIG. 3, a small volume of liquid extractant, e.g., 5 ml, is injected into the portable HTLAAS 30 via the air inlet slot 32. The air pump 34 is then actuated so as to draw air via an asymmetric air inlet 32 and upwardly in a swirling path through an open sampling tube, with part of said air impinging upon liquid that is collected beneath inlet 32 so as to cause a part of that liquid to spread as a moving film over the interior surface of said sampling tube and thereby assure full wetting of said surface and efficient analyte transfer from the air to the extractant. The highly turbulent and swirling motion of the inrushing air causes the injected liquid extractant to collect from the air a substantial fraction of air contaminants, including vapors and aerosols in the respirable size range of 0.3–5 microns. After sampling the air for a measured length of time, e.g., for 1–5 minutes, the air pump is shut off, and the liquid extractant is allowed to drain through a stopper 35 into a collecting vial 36, from which it can be transferred to an analyzer or an indicator tape (not shown).

The ability of the HTLAAS to collect both vapors and aerosols from the sampled air should be especially useful in applications where a significant fraction of the airborne analyte may be in vapor form (e.g., organo-metallic compounds, such as methyl mercury or tetraethyl lead) or in liquid droplets.

Figure 4:
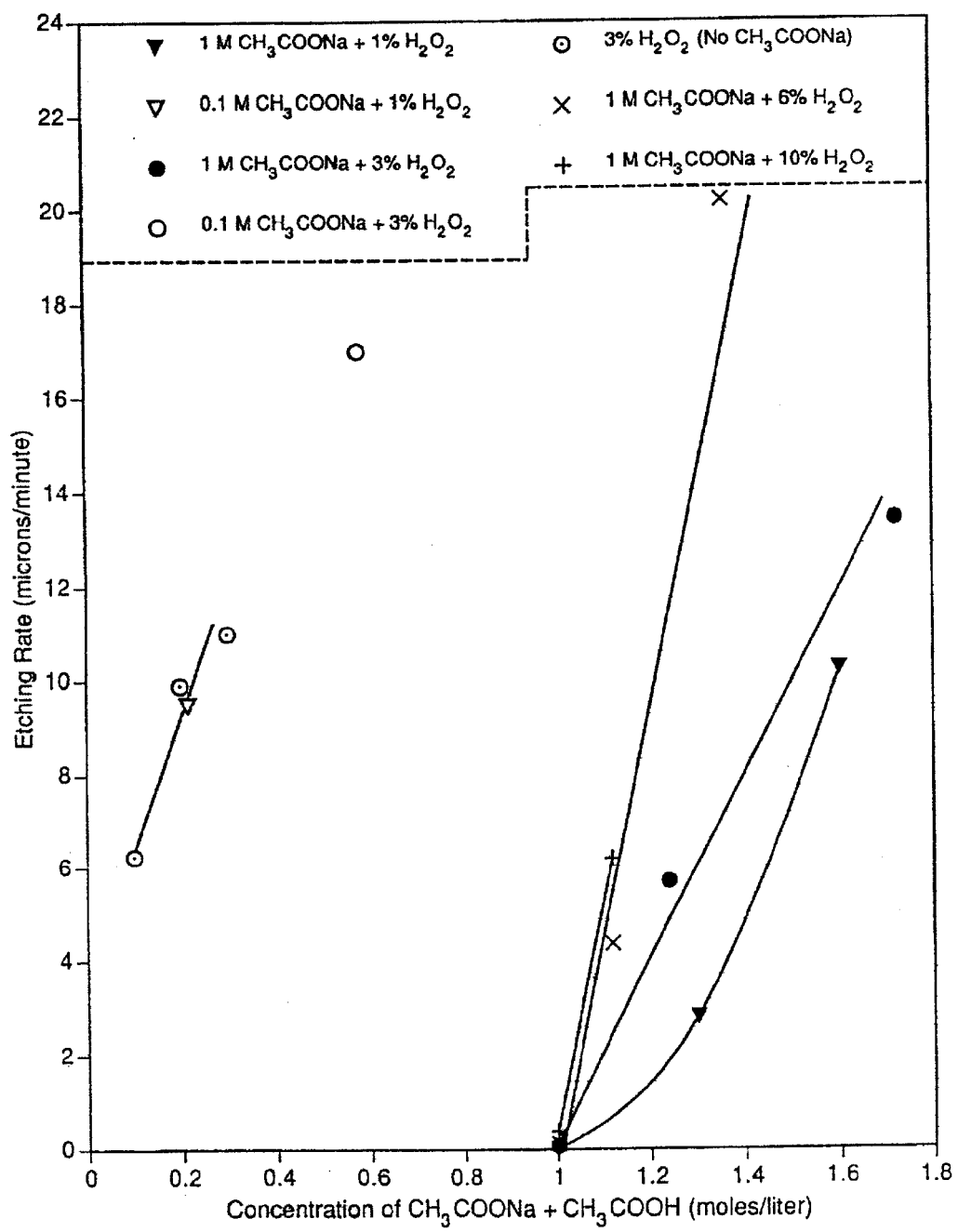
FIG. 4 shows the variation in the rate of dissolution of metallic lead at 20° C. with the concentrations in water of acetic acid plus acetate ions and of hydrogen peroxide.
Figure 5:
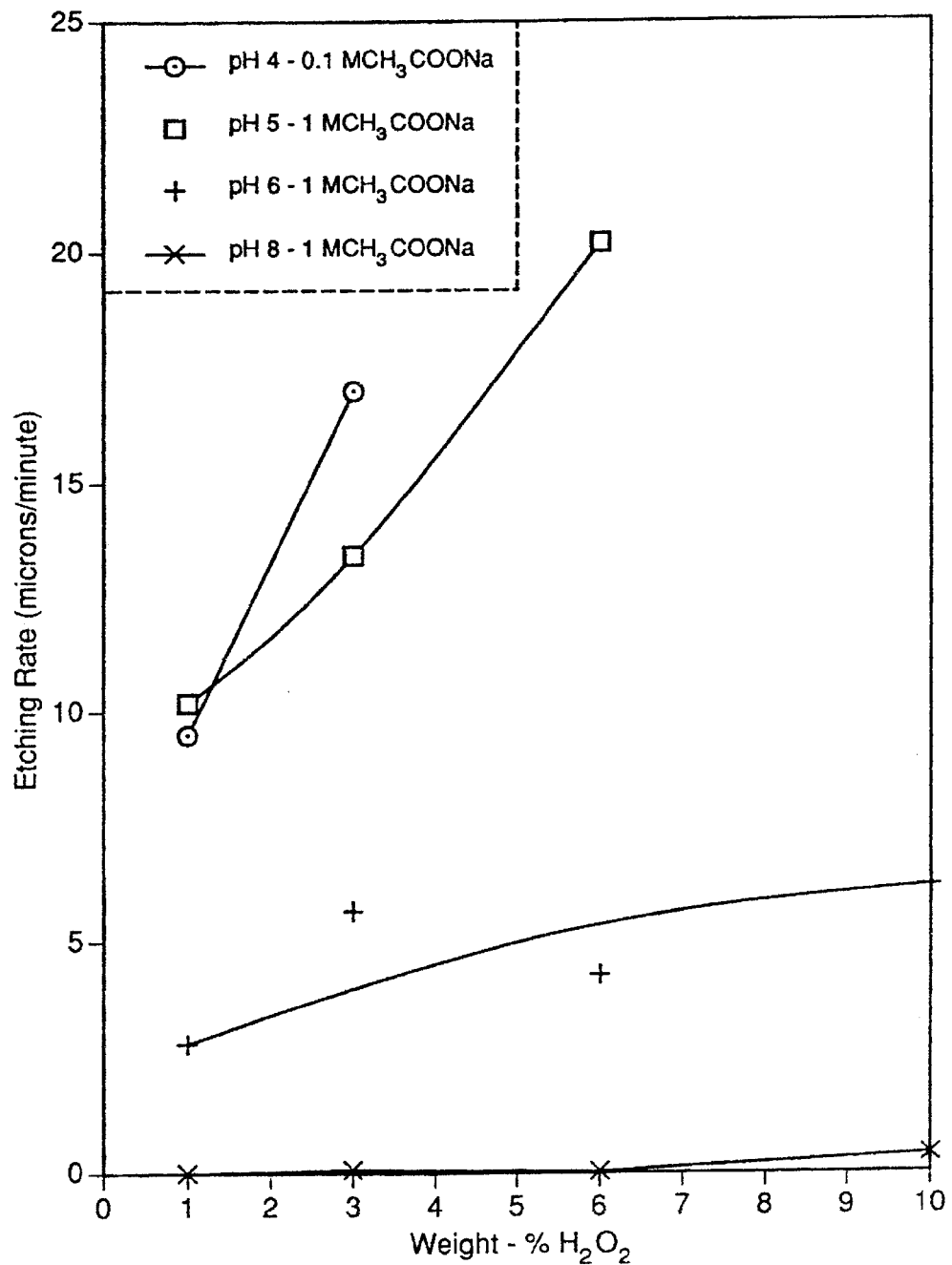
FIG. 5 shows the effects of pH and hydrogen peroxide concentration on the rate of dissolution of lead in solutions of 0.1 M and 1 M of sodium acetate.
Figure 6:
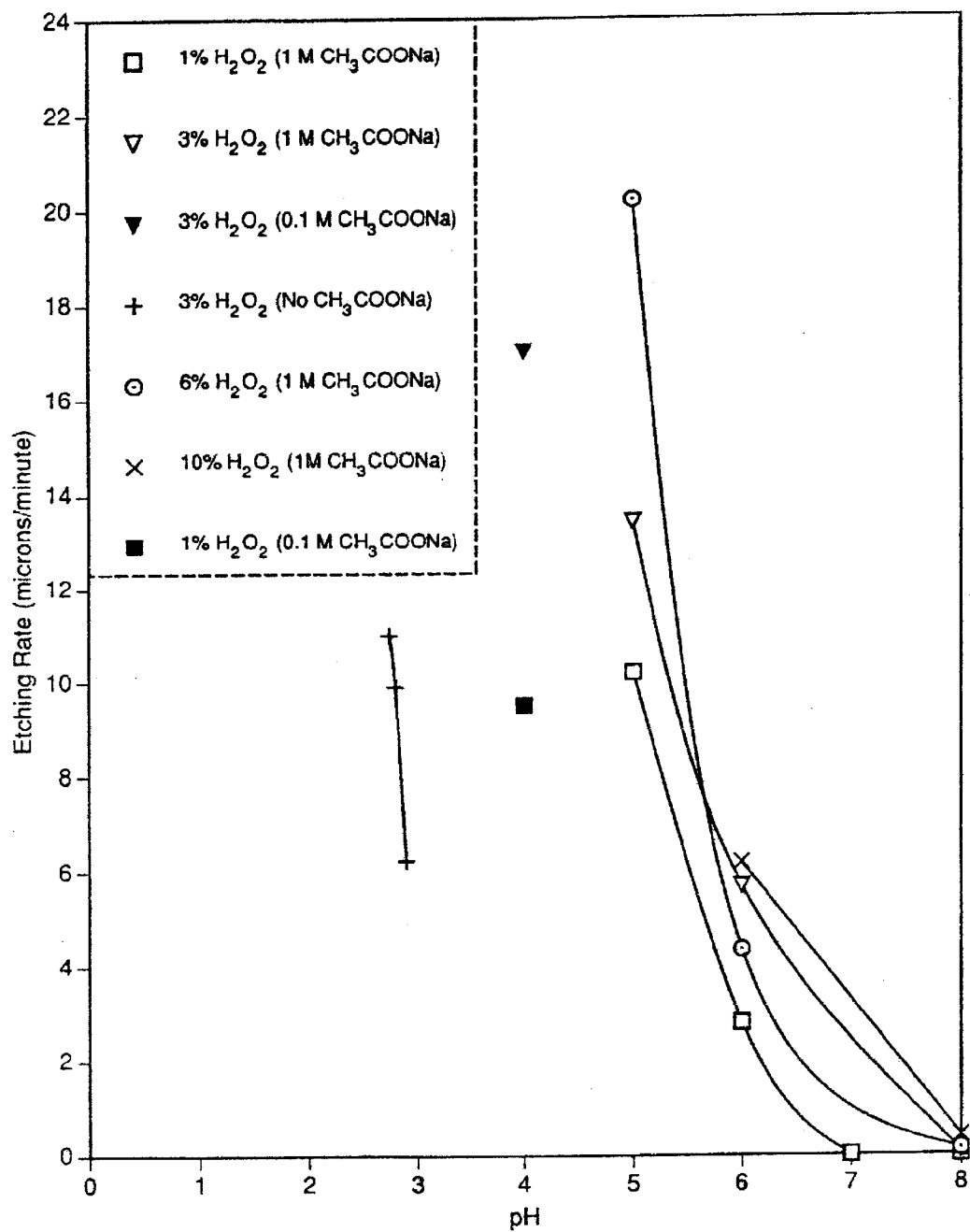
FIG. 6 shows the effect of pH on the dissolution rate of lead in solutions of 1 M or 0.1 M of sodium acetate or of 0.1 to 0.3 M of acetic acid plus 1–10% of hydrogen peroxide.

The extractant that is to be used in either of the embodiments of FIGS. 2 and 3 will depend on the analyte of interest. To dissolve lead compounds, such as lead oxide (PbO), lead carbonate ($PbCO_3$), or lead nitrate ($Pb(NO_3)_2$), a solution of acetic acid or acetate may suffice. To solubilize metallic lead, an oxidant needs to be added to the extractant. The effect of pH and of acetic acid, acetate, and oxidant concentrations in water on the rate of solubilization of metallic lead at 20° C. is shown in FIGS. 4–6. At a pH of 5 or less, as little as 0.1 M of sodium acetate or acetic acid plus 1 weight-% $H_2O_2$ suffices to yield an etching rate of about 10 microns/min, which implies that particulates in the respirable size range of <5 microns will completely dissolve in such a solution within a fraction of a minute.

Indeed, when 1-mL portions of an extractant containing 0.3 M acetic acid plus 3% hydrogen peroxide were added to 1-mg samples of powdered lead carbonate (passed through a 325×325 mesh gauze that retained particles of sizes >40 microns), lead oxide, or lead nitrate, complete dissolution of the powders occurred within less than a minute. It therefore appears that a solution containing 0.1–1 M of acetic acid or acetate ions plus 1–10% of hydrogen peroxide is adequate for the solubilization of lead-containing particulates, provided that its acidity is kept at a pH of 5 or less. Furthermore, for use with the HTLAAS (FIG. 3), the preferred concentration range is 0.1–0.3 M of acetic acid plus acetate ions and 1–3% of hydrogen peroxide.

If it is desired to monitor solely the lead content of respirable particulates, a coarse filter or filter-tape may be interposed at the air intake 7 of FIG. 2 or 32 of FIG. 3, so as to exclude the non-respirable particulates from the collected samples.

The analyzer 25 of FIG. 2 or an equivalent analytical means that is to be used with vial 36 of FIG. 3 will again depend on the analyte of interest. For the detection of lead in aqueous solutions under field conditions, a colorimetric or electro-analytical method appears to be more cost effective than either of the afore-mentioned methods based on atomic absorption spectroscopy (NIOSH Method 7082) or X-ray fluorescence.

A simple and rapid colorimetric method for estimating lead concentrations in aqueous solutions consists of placing a droplet of the test solution on a lead indicator tape or strip, such as the commercially available "EM Quant Lead Test" strips from EM Science (Gibbstown, N.J. 08027, Catalog No. 10077-1) that are distributed by Alfa/Johnson Matthey (Ward Hill, Mass. 01835, Catalog No. 34933). These strips can be used directly with the extractant, without any intermediate steps. By comparing the color of the wetted strip with a color-comparison chart, one obtains an estimate of lead concentrations in the range of 15–500 ppmw (parts per million by weight). There is no interference from either the acetic acid or the hydrogen peroxide in the extractant.

A far more sensitive and more accurate quantitative detection method for dissolved lead in an aqueous electrolyte is anodic stripping voltammetry (ASV), as described, for instance, by DeAngelis et al. in *Anal. Chem.*, 48(14): 2262–2263 (1976) and 49(12):1792–1797 (1977). The supporting electrolyte was 1 M potassium acetate adjusted to pH 4.0 with acetic acid, which is fully compatible with the afore-disclosed liquid extractant. A portable instrument based on ASV and on the work of Gunasingham et al., *J. Electroanalytical Chemistry*, 186:51 (1985),—the Electrascan ECF1-Pb—permits rapid and fairly accurate measurements of lead concentrations in the switchable ranges of 50–700 ppbw (parts per billion by weight) and 500–3,000 ppbw.

An alternative electro-analytical detection method could be based on a lead-sensitive ion-selective electrode (ISE) whose LDL for lead ions in acetate buffer was found by Heine et al., *Anal. Chim. Acta*, 100:193–205 (1978), to vary between $10^{-8}$ M and $3\times10^{-7}$ M (corresponding to 2–60 ppbw). Such a method would be most attractive for field use if the ISE can be rendered insensitive to commonly encountered interferences.

The measurement time by either of the afore-mentioned calorimetric or electroanalytical methods is usually of the of the order of 1 minute.

To evaluate the effectiveness of the systems of FIGS. 2 and 3, it is helpful to consider a few numerical examples. Thus, in the embodiment of FIG. 2, the MiniKap 500 cartridge retains all particles >0.2 micron in size and accepts air flows of 130 L/min. Assuming that particles of up to 0.2 micron make up <20 weight-% of the airborne particulates, the collection efficiency of the cartridge will be >80%. Therefore air containing $5\times10^{-5}$ g Pb/m$^3$ and flowing at a rate of 130 L/min will yield at least $$0.80\times130 \text{ (L/min)}\times5\times10^{-5} \text{ (g Pb/m}^3)/1{,}000 \text{ (L/m}^3)=5.2\times10^{-6} \text{ g Pb/min}.$$

After 1 minute's sampling time, the collected lead can be dissolved in a volume of extractant that equals the hold-up volume of the filter cartridge, i.e., 37 mL. This will yield a lead concentration of $5.2\times10^{-6}$ g/37 mL=$1.4\times10^{-7}$ g/mL or 140 ppbw, which is within the range of 50–700 ppbw that is measurable with the Electrascan ECF1-Pb. The same range of 50–700 ppbw will also permit measurements of airborne lead concentrations as low as $10^{-5}$ g/m$^3$ using a 2-minute collection time. On the other hand, the other switchable Electrascan range of 500–3000 ppbw permits measurement of maximum airborne lead concentrations of about $10^{-3}$ g/m$^3$ with a 1-minute collection time at a sampling rate of 130 L/min or of $5\times10^{-3}$ g/m$^3$ with a reduced sampling rate of 30 L/min. These maximum concentrations could be increased by further reducing the air sampling rate and/or the sampling time.

Similarly, in the embodiment of FIG. 3, the portable HTLAAS sampling air containing $5\times10^{-5}$ g Pb/m$^3$ at a rate of about 300 L/min for 1 minute at a collection efficiency of 20% will yield $$0.20\times5\times10^{-5} \text{ (g Pb/m}^3)\times300 \text{ (L/min)}\times1 \text{ min}/1{,}000 \text{ (L/m}^3)=3\times10^{-6} \text{ g Pb},$$

which, upon dissolution in about 5 mL of liquid extractant, yields a lead concentration of 600 ppbw. This concentration falls within the 500–3000 ppbw range that is measurable with the Electrascan ECF1-Pb. Alternatively, if the concentration of airborne lead is in excess of $3\times10^{-4}$ g/m$^3$ and the sampling time is increased to 5 min or the liquid volume reduced to 1 mL, the EM Quant test strips could be used for a quick estimation of the airborne lead concentration.

Either of the embodiments of FIGS. 2 and 3 has thus been shown to require sampling and measurement times at least 10 times shorter than are needed by the afore-mentioned NIOSH or X-ray fluorescence methods. Moreover, the system of FIG. 3 permits monitoring of several locations in a lead-contaminated area, such as a firing range, with a single portable unit. Furthermore, since the components of FIG. 3 are quite inexpensive, it will probably be far less costly to install 10 such units in various locations than to install a single X-ray fluorescence spectrometer. The approach disclosed herein therefore offers a far more cost-effective solution to the lead-monitoring problem than what is presently available.

The selection of an appropriate analyzer for lead in aqueous solutions, whether colorimetric or electroanalytical, will depend on specific application needs. For instance, a satisfactory lead-sensitive ISE would be especially advantageous for field use because of its simplicity, low cost, and portability. However, any Pb-responsive ISE must be rendered compatible with the selected liquid extractant, insensitive to expected interferences (e.g., copper or calcium ions), and yet sensitive to about $10^{-6}$ g Pb/mL. The accuracy and reliability of any selected candidate ISE must be tested for various concentrations of lead and of likely interferences.

The complete instrumentation of either FIG. 2 or 3 is preferably designed to not only sample air at a high throughput, collect the airborne lead at an acceptable efficiency, dissolve the collected lead in the liquid extractant, and measure the lead content of the extractant, but also to translate the measured value into the concentration of airborne lead, record the concentration-time profile, and sound an alarm when the concentration is in excess of a predetermined level. The instrumentation may include a visual (e.g., flashing lights) and/or acoustic (siren, whistle, or voice recording) alarm or merely an alarm-triggering circuit (not shown).

The high-throughput devices of FIGS. 2 and 3 permit rapid and cost-effective estimates of airborne lead concentrations under field conditions and will thereby help to prevent or minimize personnel exposure to hazardous concentrations of lead. The system of FIG. 2 may be automated or semiautomated by inclusion of a microprocessor- or microcomputer-controller (not shown).

There will now be obvious many variations and modifications of the afore-disclosed embodiments to persons skilled in the art. Although the preferred embodiments are addressed primarily to lead monitoring, it will be obvious that similar approaches can apply to the monitoring of other hazardous substances, e.g., comprising cadmium, zinc, chromium, uranium, or compounds of these metals, miscellaneous carcinogens, and other toxic contaminants, that can be either absorbed directly in a suitable liquid extractant or solubilized therein from collected airborne particulates. All of these variations and modifications will remain within the scope of this invention if defined by the following claims.

What is claimed is:

1. In apparatus for monitoring the concentration of an airborne analyte appertaining the family of substances comprising lead, cadmium, zinc, chromium, uranium, or compounds of these metals, miscellaneous carcinogens, and other toxic contaminants, the improvement comprising:

a substantially gas- and liquid-impermeable container means;

means for introducing a substantially analyte-free liquid extractant into said container means;

means for rapidly sampling ambient air and collecting particulates therefrom into said liquid extractant, said sampling means comprising an air intake means and and an air venting means;

means for solubilizing the analyte contained in said particulates into a volume of liquid extractant, wherein said sampling means and said solubilizing means are both within the same enclosure and combined in a single device;

means for removing from said container means an analyte-enriched liquid extractant; and means for estimating the concentration of the analyte in said analyte-enriched liquid extractant, wherein said sampling and collecting means comprises a filter module for collecting the particulates and solubilizing the analyte and said estimating means comprises means for pumping analyte-enriched extractant out of said module, and feeding a portion of said enriched extractant to an analyzer.

2. In apparatus for monitoring the concentration of an airborne analyte appertaining to the family of substances comprising lead, cadmium, zinc, chromium, uranium, or compounds of these metals, miscellaneous carcinogens, and other toxic contaminants, the improvement comprising;

a substantially gas- and liquid-impermeable container means;

means for introducing a substantially analyte-free liquid extractant into said container means;

means for rapidly sampling ambient air and collecting particulates therefrom into said liquid extractant, said sampling means comprising an air intake means and and an air venting means;

means for solubilizing the analyte contained in said particulates into a volume of liquid extractant, wherein said sampling means and said solubilizing means are both within the same enclosure and combined in a single device;

means for removing from said container means an analyte-enriched liquid extractant; and means for estimating the concentration of the analyte in said analyte-enriched liquid extractant, comprising a portable liquid-absorption air sampler for collecting the particulates and solubilizing the analyte, wherein said volume of air passes through said sampler in a swirling and highly turbulent motion through an asymmetric air inlet and upwardly in a swirling path through an open sampling tube, with part of said air impinging upon liquid that is collected beneath said inlet so as to cause a pail of that liquid to spread as a moving film over the interior surface of said sampling tube and thereby assure fill wetting of said surface, and efficient analyte transfer from the air to the extractant.

3. The improvement of claim 2, wherein said solubilizing means includes a liquid extractant comprising acetate ions for dissolving lead-containing analytes.

4. The improvement of claim 2, wherein said means for estimating the concentration is a colorimetric or electroanalytical device.

5. The improvement of claim 4, wherein said colorimetric device is an analyte-indicating tape or strip.

6. The improvement of claim 4, wherein said electroanalytical device is an anodic stripping voltammetry instrument.

7. The improvement of claim 4, wherein said electroanalytical device is an analyte-responsive ion-selective electrode.

8. In a method for monitoring the concentration of an airborne analyte appertaining to the family of substances comprising lead, cadmium zinc, chromium, uranium, or compounds of these metals, miscellaneous carcinogens, and other toxic contaminants the improvement comprising the steps of:

providing a substantially gas- and liquid-impermeable container means;

introducing a substantially analyte-free liquid extractant into said container means;

passing ambient air through an inlet opening into said container means and collecting particulates in said liquid extractant within a particulate-retaining means;

solubilizing the analyte from the collected particulates into a volume of liquid extractant within said retaining means; and measuring the concentration of the analyte in the liquid extractant.

9. The method of claim 8, wherein said passing, collecting, solubilizing, and measuring steps comprise passing a volume of sampled air through a filter module so as to retain particulates from the air;

solubilizing the analyte from the retained particulates by soaking the filter in the extractant;

pumping analyte-enriched extractant out of said module; and feeding a portion of said enriched extractant to an analyzers.

10. The improvement of claim 8, wherein the concentration of the analyte is measured by a colorimetric or an electro-analytical method.

11. The improvement of claim 8 which comprises:

passing sampled air in a swirling and highly turbulent motion through a portable liquid-absorption air sampler so as to cause particulates from the sampled air to be retained and wetted at the inner walls of the sampler;

causing the retained particulates to be carried down by the liquid extractant and thereby solubilize the analyte from the particulates into a volume of analyte-enriched extractant; and collecting the analyte-enriched extractant and measuring the analyte concentration therein.

12. The improvement of claim 11, wherein at least part of the analyte is in the form of vapor or is contained in liquid droplets, and the extractant is caused to pick up the vapor or droplets at the inner walls of the sampler.

13. The improvement of claim 11, wherein at least part of the analyte is in the form of a metal and said extractant comprises an oxidant that is able to oxidize said metal.

14. The improvement of claim 8, wherein said liquid extractant comprises acetate ions for dissolving lead-containing analytes.

15. The improvement of claim 14, wherein said extractant is an aqueous solution having a pH of 5 or less.

16. The improvement of claim 15, wherein the concentration of acetate ions plus acetic acid is in the range of 0.1–1 N.

17. The improvement of claim 16, wherein said extractant comprises an oxidant that can oxidize metallic lead.

18. The improvement of claim 17, wherein said oxidant is hydrogen peroxide.

19. The improvement of claim 18, wherein the concentration of hydrogen peroxide is in the range of 1–10 weight-%.

* * * * *